US00PP11515P

United States Patent [19]

Engelke

[11] Patent Number: Plant 11,515

[45] Date of Patent: Sep. 19, 2000

[54] ZOYSIA GRASS PLANT NAMED 'PALISADES'

[75] Inventor: Milton Charles Engelke, Parker, Tex.

[73] Assignee: Texas A&M University System, College Station, Tex.

[21] Appl. No.: 09/078,184

[22] Filed: May 13, 1998

[51] Int. Cl.[7] ..... A01H 5/00

[52] U.S. Cl. ..... Plt./390

[58] Field of Search ..... Plt./390, 388

[56] References Cited

U.S. PATENT DOCUMENTS

P.P. 9,127 5/1995 Gibeault et al. ..... Plt./390

OTHER PUBLICATIONS

R.H. White, M.C. Engelke and S.J. Morton, Performance of Zoysiagrass Cultivars and Elite DALZ Lines Under Linear Gradient Irrigation, TX Turfgrass Res.—1990, Consolidated Prog. Rep. PR–4748: 33–36.

M.C. Engelke, R.H. White, S. J. Morton and K.B. Marcum, Root Development in Selected Varieties of Each of Four Warm–season Turfgrass Genera, TX Turfgrass Res.—1991, Consolidated Prog. Rep. PR–4884: 10–17.

S.J. Morton, M.C. Engelke, R.H. White and K.B. Marcum, 1991 Update on Performance of Zoysiagrass Cultivars and Elite DALZ Lines Under Linear Gradient Irrigation. TX Turfgrass Res.—1991, Consolidated Prog. Rep. PR–4890: 36–42.

S.J. Morton, M.C. Engelke and R.H. White, Performance of Four Warm–season Turfgrass Genera Cultured in Dense Shade iii. Zoysia spp., TX Turfgrass Res.—1991, Consolidated Prog. Rep. PR–4894: 51–52.

USDA–NTEP. 1991 National Zoysiagrass Test–1991. U.S. Dept. Agric. Beltsville, MD. 1995 Prog. Rept., NTEP No. 96–6: 54 pp.

USDA–NTEP. 1991 National Zoysiagrass Test–1991, U.S. Dept. Agric. Beltsville, MD. Final Report 1992–95, NTEP No. 96–15:101 pp.

USDA–NTEP. 1991. National Zoysiagrass Test–1991, U.S. Dept. Agric. Beltsville, MD 1993 Pro. Rept., NTEP No. 94–5: 54 pp.

USDA–NTEP. 1991. National Zoysiagrass Test–1991, U.S. Dept. Agric. Beltsville, MD 1994 Prog. Rpt. NTEP No. 95–8: 66 pp.

K.B. Marcum and M.C. Engelke, Root Development of Zoysiagrasses Included in the 1991 National Turfgrass Evaluation Program Trial. TX Turfgrass Res.—1992, Consolidated Prog. Rep. PR–4978:2–4.

S.J. Morton, M.C. Engelke, R.H. White and K.B. Marcum, Summarization of Zoysiagrass Performance Under Linear Gradient Irrigation, TX Turfgrass Res.—1992, Consolidated Prog. Rep. PR–4989: 38–44.

S.J. Morton and M.C. Engelke. 1993. Zoysiagrass Entries in the 1991 National Turfgrass Evaluation Program Trial at Dallas. TX Turfgrass Res.—1994, Consolidated Prog. Rep. PR–5110: 18–21.

S.J. Morton and M.C. Engelke, Performance of Three Warm–Season Turfgrass Genera Cultured in Shade iii. TX Turfgrass Res.—1994. Consolidated Prog. Rep. PR–5139: 102–104.

K.B. Marcum, M.C. Engelke, S.J. Morton and C. Dayton, Salinity Tolerances of Selected Bermudagrass and Zoysiagrass Genotypes. TX Turfgrass Res.—1994, Consolidated Prog. Rep. PR–5140: 105–107.

S.J. Morton and M.C. Engelke, Update to the 1991 National Turfgrass Evaluation Program (NTEP) Zoysiagrass Trial at TAES–Dallas. TX Turfgrass Res.—1994, Consolidated Prog. Rep. PR–5239: 10–12.

S.J. Morton, M.C. Engelke and K.G. Porter, Performance of Three Warm–Season Turfgrass Genera Cultured in Shade iii. Zoysia spp. TX Turfgrass Res.—1994, Consolidated Prog. Rep. PR–5242: 27–29.

S.K. Riffell, M.C. Engelke and S.J. Morton, 1995 Update to the 1991 National Turfgrass Evaluation Program (NTEP) Zoysiagrass Trial at TAES–Dallas. TX Turfgrass Res.—1995. Consolidated Prog. Rep. TURF –95–5: 26–33.

S.K. Riffell, M.C. Engelke and S.J. Morton, Performance of Three Warm–Season Turfgrasses Cultured in Shade: Zoysiagrass. TX Turfgrass Res.—1995. Consolidated Prog. Rep. TURF–95–11: 60–65.

I. Yamamoto and M.C. Engelke, Establishment of Warm–Season Turfgrasses by Three Vegetative Propagation Methods. TX Turfgrass Res. —1996. Consolidated Prog. Rep. TURF–96–4: 22–28.

I. Yamamoto and M.C. Engelke,. 1996 Update of Zoysiagrass Performance under 90% Shade Conditions. TX Turfgrass Res.—1996. Consolidated Prog. Rep. TURF–96–11: 65–72.

James A. Reinhart, M.C. Engelke and Sharon J. Morton, Zoysiagrass Resistance To The Zoysiagrass Mite, Eriophyes Zoysiae (Acari: Eriophyidae), 1993, Inter. Turfgrass Soc. Res. J. 7: 349–352.

R.H. White, M.C. Engelke, S.J. Morton and B.A. Ruemmele, Irrigation Water Requirement of Zoysiagrass, 1993, Inter. Turfgrass Soc. Res. J. 7:587–593.

S.K. Braman, A.F. Pendley, R.N. Carrow and M.C. Engelke, Potential Resistance In Zoysiagrasses To Tawny Mole Crickets (Orthoptera: Gryllotalpid), 1994, Fl. Entomol. 77(3): 301–305.

J.A. Reinert, M.C. Engelke, J. C. Read, S.J. Maranz and B.R. Wiseman, Susceptibility Of Cool And Warm Season Turfgrasses To Fall Armyworm, *Spodoptera Frugiperda.*, 1997, In R. M. Martin, et al. (eds.) Int. Turfgrass Soc. Res. J. 8: 1003–1011.

Y.L. Qian and M.C. Engelke, Evaluation of Zoysiagrass Genotypes for Shade Tolerance. TX Turfgrass Res.—1997. Consolidated Prog. Rep. TURF–97–24: 11p.

(List continued on next page.)

*Primary Examiner*—Howard J. Locker
*Assistant Examiner*—Wendy A Baker
*Attorney, Agent, or Firm*—Fulbright & Jaworski L.L.P.

[57] ABSTRACT

An asexually reproduced variety of perennial *Zoysia japonica* with a unique combination of characters including white stigmas, and anthers are 5.0 RP 3/6.

2 Drawing Sheets

OTHER PUBLICATIONS

Y.L. Qian and M.C. Engelke, National Turfgrass Evaluation Program, (NTEP) Zoysiagrass Trial at TAES–Dallas, 1996 Consolidated Prog. Rep. TUR–F 97–29: 5p.

M.H. Hall, R.H. White, J.E. Gaudreau, W.G. Menn and G.R. Taylor. Zoysiagrass Cultivar Study. Consolidated Prog. Rep. TURF–97–33: 6p.

J.A. Reinert and M.C. Engelke. Resistance in Zoysiagrass (Zoysia spp.) to the Tropical Sod Webworm (*Herpetogramma phaeopteralis*), TX Turfgrass Res.—1992, Consolidated Prog. Rep. PR–4996: 54–55.

J.A. Reinert, M.C. Engelke, and S.J. Morton. Zoysiagrass Resistance to the Zoysiagrass Mite, *Eriophyes zoysiae* (Acari: Eriophyiadae). TX Turfgrass Res.—1994, Consolidated Prog. Rep. PR–4997: 55–57.

S.J. Morton, M.C. Engelke and J.A. Arnau. Photoperiod Effects on Flowering in Zoysia. TX Turfgrass Res.—1997. Consolidated Prog. Rep. TURF–97–25.

BRIEF SUMMARY OF THE INVENTION

The present invention relates to a new and distinct asexually reproduced variety of perennial zoysiagrass (*Zoysia japonica* (L.)) Merr.

BACKGROUND OF THE INVENTION

This invention relates to an new and distinct perennial zoysiagrass cultivar indentified as 'Palisades' zoysiagrass (herein referred to as 'Palisades'), that was tested as DALZ8514. 'Palisades', a *Zoysia japonica*, is a chance hybrid of the maternal clone 'Z44', obtained from Beltsville, MD in 1981, with an unknown pollen source from a zoysiagrass germplasm field nursery at TAES—Dallas. 'Palisades' has been vegetatively propagated, and is uniform in growth expression.

For purposes of registration under the "International Convention for the Protection of New Varieties of Plants" (generally known by its French acronym as the UPOV Convention) and noting Section 1612 of the Manual of Plant Examination Procedures, the new variety of zoysiagrass of the present invention is named 'Palisades' Zoysiagrass.

BRIEF DESCRIPTIONS OF THE ILLUSTRATIONS

DETAILED DESCRIPTION OF THE PLANT

Figure 1:
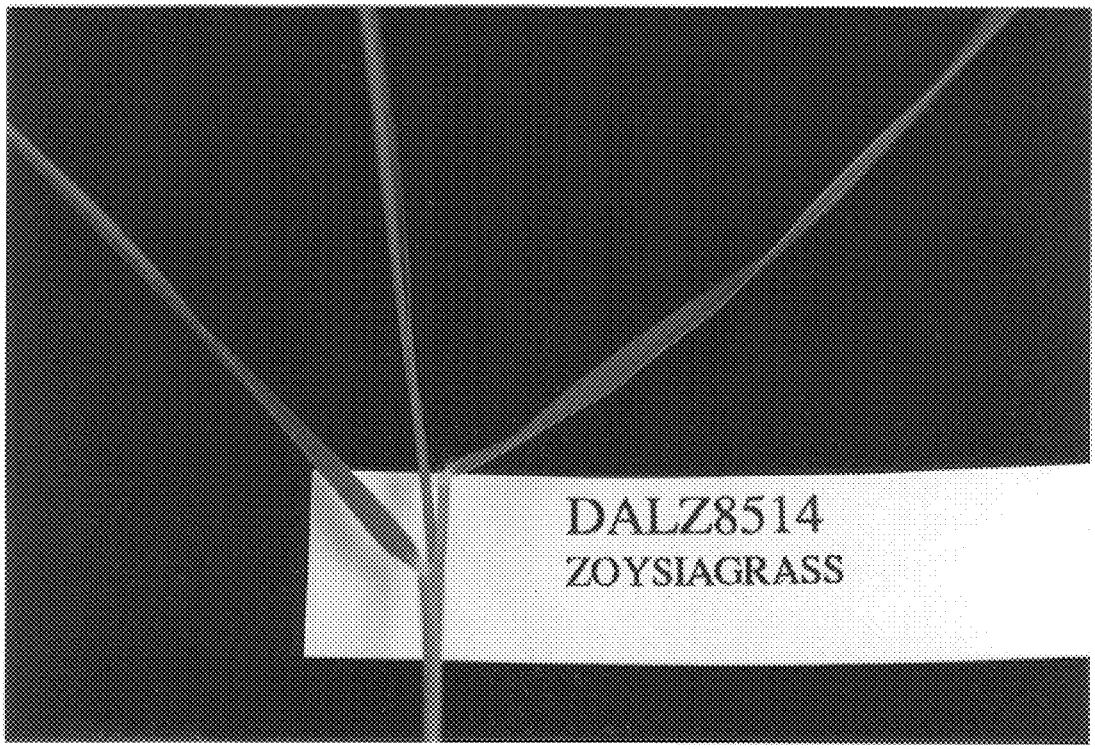
FIG. 1 is a photograph of the leaf orientation, blades and ligule of 'Palisades'.
Figure 2:
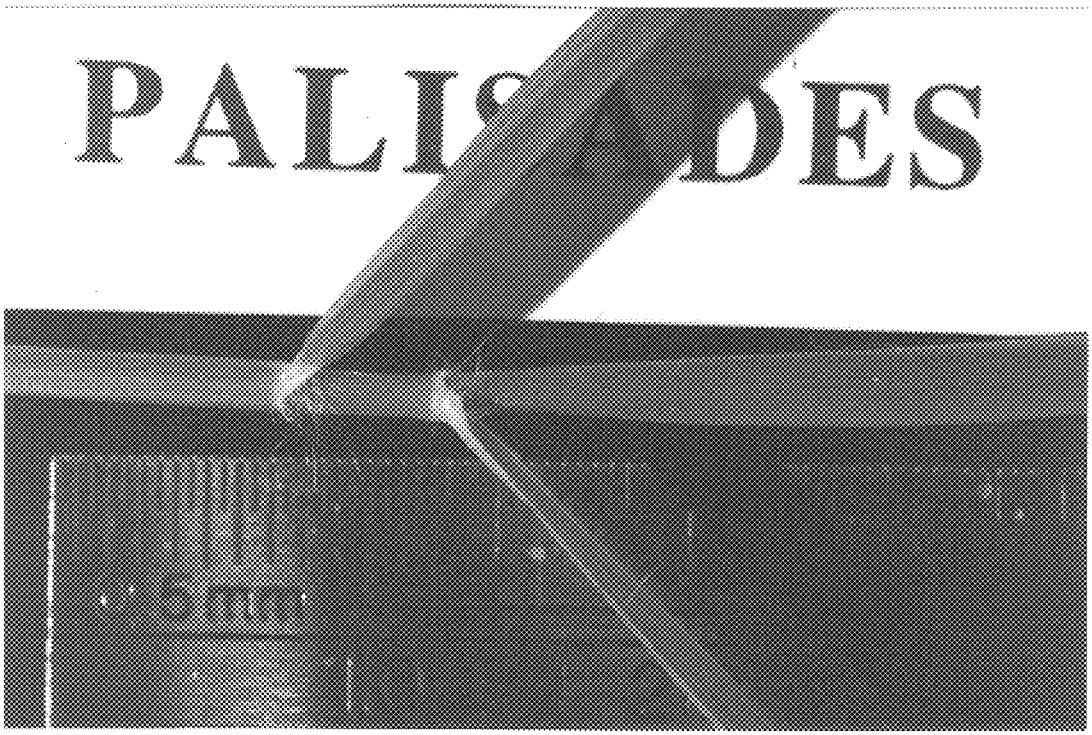
FIG. 2 is a close-up photograph of the leaf orientation, blades and ligule of 'Palisades'.
Figure 3:
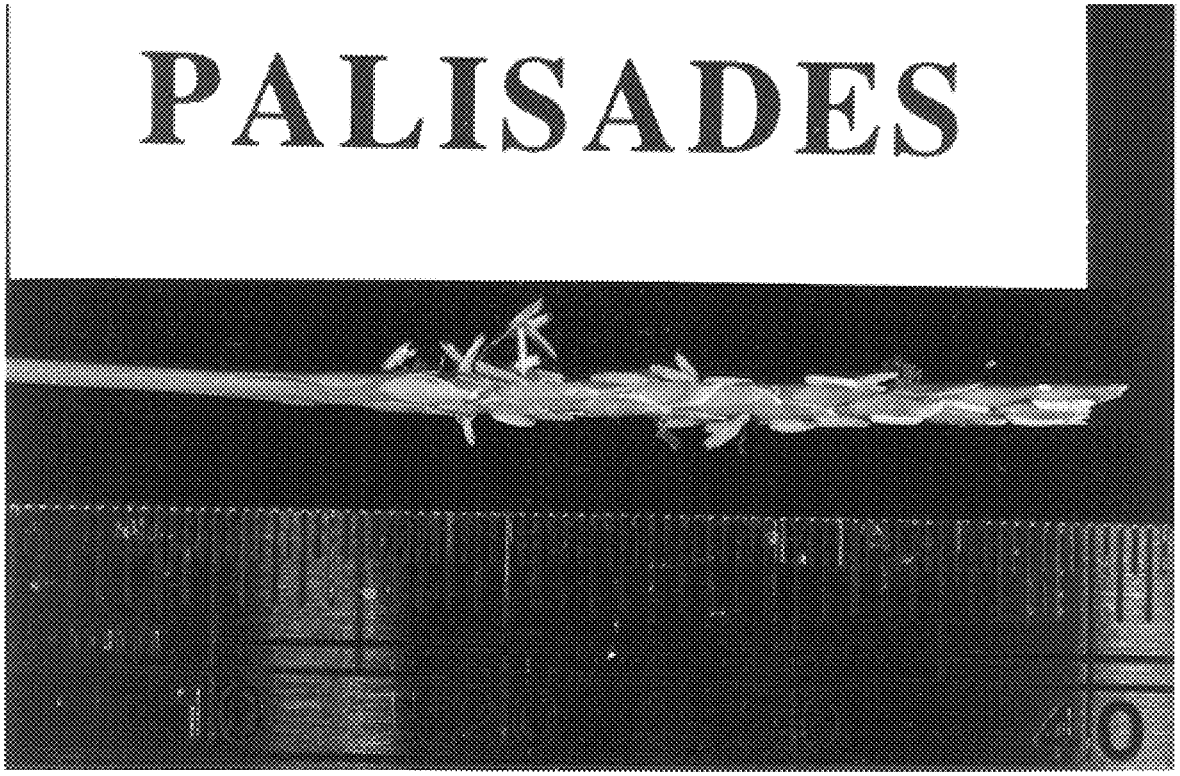
FIG. 3 is a photograph of the in florescence of 'Palisades' at anthesis.

'Palisades' was characterized in greenhouse and field conditions. 'Palisades' is a unique variety of zoysiagrass developed as described above. 'Palisades' was identified as being unique and desirable and was then propagated by cutting of stolons and rhizomes, rooting them in soil, and planting of the rooted material to provide planting stock for studying performance and for comparison of morphological characters after propagation. 'Palisades' has been propagated by sod, plugs, sprigs, stolons and rhizomes in greenhouse and field planting by hand and mechanical propagation in Dallas, Tex. and is uniform in growth expression. Seed reproduction with self-fertility is not common in the Zoysia sp. No seedling establishment from 'Palisades' has been noticed in either greenhouse or field studies.

'Palisades' is asexually propagated by stolons and rhizomes. It has an intermediate to rapid establishment rate. When spring (stolons) or plug plantings are made in early May, the area should achieve 60–70% coverage in Dallas, Tex. in 90–120 days, with complete coverage in 180–200 days, in comparison to 'Meyer' zoysiagrass which will require 360–400 days for full coverage. The stolons of 'Palisades' have a mean internode length of 29.9 mm between the second and third nodes, with a mean internode width of 1.0 mm and node diameter of 1.7 mm (Table 1). The stolons of 'Palisades' root adventitiously at the nodes. Color notations of plant tissues were based on the Munsell *Color Charts for Plant Tissues*, Munsell Color, Baltimore, Md., 1977. Light quality, photoperiod, and general growth of the plants affect color notations. The internode stolon color of 'Palisades' stolons exposed to full sun is 5R 3/4.

Leaf blades of 'Palisades' are rolled in the bud, and are flat and stiff. The mean leaf blade length of 'Palisades' is 75.6 mm and average width is 3.4 mm (Table 2). The leaf sheath of 'Palisades' is distinct from 'Meyer'(unpatented) and 'Crowne' (U.S. Plant Patent application Ser. No. 09/076,973 at a length of 51.2 mm (Table 3). The hairs on the abaxial leaf surface of 'Palisades' are sparse in number and are approximately 0.9 mm long. Measured under greenhouse conditions in January 1996, the genetic, adaxial leaf color of 'Palisades' is 2.5G 5/6 with 'El Toro' (U.S. Plant Pat. No. 5845) having a leaf color of 2.5GY 5/2, and 'Meyer' having a color of 2.5G 3/4. The ligule of 'Palisades' is a fringe of silky hairs, approximately 2.8 mm in length for the longest hairs.

'Palisades' has 5RP 3/6 colored anthers and white colored stigmas, undistinguished in shade of color. The inflorescence of 'Palisades' is a terminal spike-like raceme, with spikelets on short pedicels. 'Palisades' has a mean length floral region of 27.2 mm, with a mean of 27.8 florets per raceme.

Thatch development is a function of age of stand, types of soils and other environments and cultural conditions. Thatch development was determined in 3 year old field plantings comparing eight commercially available cultivars. 'Emerald', 'Miyako' (U.S. Plant Pat. No. 10,187) and 'Zeon' (unpatented) produced the greatest depth of thatch (26.3 mm); 'Crowne', 'Palisades' and 'DeAnza' produced an intermediate amount of thatch (25,23 and 23 mm, respectively), and Cavalier and Meyer produced the least amount of thatch (20 and 19 mm respectively).

The chromosome number of 'Palisades' is 40.

'Palisades' is rated as having low supplemental water needs similar to 'Crowne' and 'El Toro' to maintain active growing turf (Table 4). When 'Palisades' was compared with 59 other zoysiagrasses for salinity tolerance, it ranked number 34 in performance and was superior to 'Meyer' (Table 5). When compared to other commercial varieties for root growth, 'Palisades' was not different from 'El Toro' or 'Meyer' in average root depth, root weight, or clipping weights (Table 6).

'Palisades' was entered in the 1991 National Turfgrass Evaluation Program (NTEP). 'Palisades', in the 1991 National Turfgrass Evaluation Program Zoysiagrass Trial for the years 1992–1995 had mean quality ratings of 5.8, 5.8, 5.5 and 5.4 for overall quality (Table 7).

'Palisades' rated among the best for the broad leaf textural class 4. 'Palisades' shows intermediate resistance to the zoysiagrass mite (Table 8). The varieties 'Meyer', 'Belair' (unpatented), and most experimental zoysiagrasses are very susceptible to the mite. This mite has been found in Maryland, Texas, and Florida, all extensive zones of use for zoysiagrasses.

'Palisades' is distinguished from other zoysiagrasses by its combined unique morphological differences in leaf width, length, and floral characters of sheath and seed head length. It is a medium-coarse textured, thick stolon, and rhizome producing grass with good recuperative ability. It has good shade tolerance and low water use needs. It is moderate in salinity tolerance. 'Palisades' is intermediate to superior in its average growth rate and has good to excellent winter hardiness and will persist in regions north to Kansas, Missouri and Illinois.

TABLE 1

Internode length as measured between the second and third nodes, internode diameter of the third internode, and node diameter of the third node measured on zoysiagrass plants. Plants were growing in a growth chamber with a 14-hr daylength, March 1995

| Genotype | Internode length mm | Internode diameter mm | Node diameter mm |
|---|---|---|---|
| 'Crowne' | 17.7a* | 0.9abc | 1.1 bc |
| 'Cavalier' (U.S. Plant Pat. No. 10,778) | 18.4a | 1.4abc | 1.4abc |
| 'Meyer' | 24.1a | 2.0a | 2.0a |
| 'Palisades' | 29.9a | 1.0a | 1.7ab |
| 'El Toro' | 39.98a | 1.4abc | 1.4abc |

*Analysis of variance by General Linear Models, with means followed by the same letter not significantly different using Tukey's Studentized Range (HSD), alpha = 0.05. Only selected means presented.

TABLE 2

Leaf blade width and length measured on the third youngest leaf of zoysiagrass. Plants were growing in a growth chamber with a 14-hr daylength, March 1995

| Genotype | Blade width mm | Blade length mm |
|---|---|---|
| 'Cavalier' | 1.3d* | 60.7cd |
| 'Meyer' | 2.6 c | 74.3 bc |
| 'Crowne' | 3.0abc | 72.7 bc |
| 'El Toro' | 3.3abc | 68.3 bcd |
| 'Palisades' | 3.4ab | 75.6 bc |

* Analysis of variance by General Linear Models, with means followed by the same letter not significantly different using Tukey's Studentized Range (HSD), alpha = 0.05. Only selected means presented.

TABLE 3

Zoysiagrass leaf sheath length measurements taken February 1988 on the fourth youngest leaf from greenhouse grown plants

| Genotype | Sheath length mm |
|---|---|
| 'Emerald'(unpatented) | 16.3 ij |
| 'Cavalier' | 28.9 ef |
| 'Meyer' | 30.7 cd |
| 'Crowne' | 42.9 b* |
| 'Palisades' | 51.25a |

*Means followed by the same letter are not significantly different using the Waller-Duncan k ratio test (k ratio = 100). Only selected means presented.

TABLE 4

Supplemental irrigation water requirement for commercial and experimental zoysiagrasses during July 1989 through August 1991 at Dallas, Texas*

| | Textural Class | Irrigation Requirement 1989 | 1990 | 1991 | Mean |
|---|---|---|---|---|---|
| | | mm/yr | | | |
| 'Diamond' (U.S. Plant Pat. No. 10,636) | 1 | 461 | 435 | 567 | 488 |
| DALZ8501 | 1 | 449 | 544 | 429 | 474 |
| FC13521 | 3 | 482 | 448 | 443 | 457 |
| DALZ8517 | 3 | 475 | 402 | 487 | 455 |
| 'Emerald' | 3 | 464 | 343 | 503 | 437 |
| DALZ8506 | 3 | 458 | 379 | 455 | 431 |
| DALZ8515 | 3 | 469 | 419 | 394 | 427 |
| DALZ8508 | 2 | 447 | 379 | 398 | 408 |
| DALZ8510 | 3 | 449 | 310 | 413 | 390 |
| 'Cashmere' U.S. Plant Pat. No. 6,529 | 1 | 435 | 424 | 311 | 390 |
| 'Cavalier' | 3 | 464 | 175 | 441 | 360 |
| DALZ8504 | 2 | 478 | 363 | 138 | 326 |
| DALZ8503 | 2 | 441 | 280 | 193 | 305 |
| DALZ8511 | 2 | 451 | 353 | 200 | 304 |
| DALZ8516 | 2 | 462 | 377 | 25 | 288 |
| 'Meyer' | 2 | 450 | 321 | 74 | 276 |
| 'Korean Common'(unpatented) | 4 | 470 | 174 | 88 | 244 |
| 'El Toro' | 4 | 417 | 21 | 6 | 148 |
| 'Palisades' | 4 | 358 | 26 | 12 | 132 |
| 'Crowne' | 4 | 256 | 12 | 12 | 93 |
| | MSD† | 129 | 169 | 242 | 155 |
| | Rainfall‡ | 1092 | 1118 | 1143 | 1118 |

†MSD, minimum significant difference for comparison of means within columns based on the Waller-Duncan k-ratio t-test where k = 100.
‡Total annual precipitation in mm.

*White et al. 1993.

TABLE 5

* Average percent shoot salt injury (average of 20 rating dates) on zoysiagrass entries in the 1991 NTEP† Trials

| Entry | Source | Species‡ | % Injury |
|---|---|---|---|
| 'Diamond' | NTEP 20 | *matrella* | 33ab£ |
| 'El Toro' | NTEP 13 | *japonica* | 38a-e |
| 'Emerald' | NTEP 10 | *jap x tenu* | 42a-h |
| 'Cavalier' | NTEP 17 | *matrella* | 42a-h |
| 'Crowne' | NTEP 15 | *japonica* | 46 e-k |
| 'Palisades' | NTEP 14 | *japonica* | 46 e-k |
| 'Belair' | NTEP 11 | *japonica* | 50 f-k |

TABLE 5-continued

* Average percent shoot salt injury (average of 20 rating dates) on zoysiagrass entries in the 1991 NTEP† Trials

| Entry | Source | Species‡ | % Injury |
|---|---|---|---|
| 'Meyer' | NTEP 09 | *japonica* | 58 lmn |
| 'Korean Common' | NTEP 07 | *japonica* | 76 pq |

* Selected data set; complete data set includes 59 varieties and cultivars.
†NTEP = National Turfgrass Evaluation Program. ‡Species identity.
£Means followed by the same letter are not significantly different, based on the Waller-Duncan k-ratio t-test (k-ratio = 100)
In Marcum, K. B., M. C. Engelke, S. J. Morton and C. Dayton. 1994. Salinity tolerances of selected bermudagrass an zoysiagrass genotypes. TX Turfgrass Res.-1993, Consolidated Prog. Rep. PR 5140: 105–107.

TABLE 6

Average mean root depth of zoysiagrass grown in flexible tubes in greenhouse studies, Dallas, TX

| Variety | Average Mean Root Depth mm | Total Root Weight mg | Clipping Weights mg |
|---|---|---|---|
| 'Cavalier' | 255 | 278 | 243 |
| 'Belair' | 296 | 330 | 286 |
| 'Palisades' | 318 | 457 | 452 |
| 'Emerald' | 330 | 461 | 241 |
| 'Meyer' | 333 | 411 | 466 |
| 'Crowne' | 355 | 497 | 406 |
| 'El Toro' | 356 | 473 | 391 |
| MSD | 79 | 161 | 267 |

*MSD = minimum significant difference for comparison of means within columns based on the Waller-Duncan k-ratio test where k = 100.
In Marcum, K. B., M. C. Engelke, S. J. Morton, and R. H. White. 1995. Rooting characteristics and associated drought resistance of zoysiagrasses. Agron. J. 87:534–538.

TABLE 7

Mean Turfgrass quality ratings of vegetative zoysiagrass cultivars grown in the National Turfgrass Evaluation Program at 23 locations in the U.S. for 1992, 1993, 1994, and 1995

| Variety | Leaf Texture Class | 1992 | 1993 | 1994 | 1995 | Overall 4-Yr Avg. |
|---|---|---|---|---|---|---|
| 'Cavalier' | 3[1] | 6.0 | 6.2 | 5.9 | 6.0 | 5.9 |
| TC2033 | 2 | 5.8 | 6.1 | 6.1 | 6.0 | 5.9 |
| 'Sunburst'(unpatented) | 2 | 5.8 | 5.9 | 5.8 | 5.9 | 5.8 |
| TC 5018 | | 5.8 | 5.8 | 5.9 | 5.7 | 5.8 |
| 'Emerald' | 2 | 5.7 | 6.2 | 6.0 | 5.7 | 5.8 |
| 'Omni'(unpatented) | 2 | 5.6 | 6.1 | 6.1 | 6.0 | 5.7 |
| QT 2004 | | 5.6 | 6.0 | 5.9 | 5.6 | 5.6 |
| DALZ8508 | 2 | 5.6 | 6.1 | 5.7 | 5.6 | 5.6 |
| 'Palisades' | 4 | 5.8 | 5.8 | 5.5 | 5.4 | 5.6 |
| DALZ9006 | 3 | 5.6 | 6.0 | 5.6 | 5.5 | 5.6 |
| 'Crowne' | 4 | 5.8 | 5.8 | 5.5 | 5.4 | 5.6 |
| 'El Toro' | 4 | 5.8 | 5.6 | 5.3 | 5.4 | 5.5 |
| CD 259-13 | | 5.3 | 5.5 | 5.7 | 5.5 | 5.4 |
| 'Meyer' | 2 | 5.3 | 5.7 | 5.8 | 5.5 | 5.4 |

TABLE 7-continued

Mean Turfgrass quality ratings of vegetative zoysiagrass cultivars grown in the National Turfgrass Evaluation Program at 23 locations in the U.S. for 1992, 1993, 1994, and 1995

| Variety | Leaf Texture Class | 1992 | 1993 | 1994 | 1995 | Overall 4-Yr Avg. |
|---|---|---|---|---|---|---|
| QT 2047 | | 5.4 | 5.4 | 5.3 | 5.2 | 5.3 |
| 'Belair' | 2 | 5.0 | 5.6 | 5.6 | 5.0 | 5.2 |
| DALZ 8516 | 2 | 4.7 | 5.4 | 5.0 | 5.0 | 4.9 |
| 'Diamond' | 1 | 4.4 | 5.0 | 4.6 | 4.4 | 4.4 |
| DALZ8501 | 1 | 4.9 | 4.3 | 4.0 | 4.0 | 4.3 |
| DALZ8701 | 1 | 4.2 | 4.1 | 3.7 | 3.6 | 3.8 |
| LSD VALUE | | 0.2 | 0.2 | 0.2 | 0.2 | 0.2 |

To determine statistical differences among entries, subtract one entry's mean from another entry's mean. Statistical difference occurs when this value is larger than the corresponding LSD value (LSD 0.05). [1]Textural class of zoysiagrass where 1 = short, narrow leaves; 2 = short, wide leaves; 3 = long, narrow leave; and 4 = long, wide leaves.
In National Zoysiagrass Test - 1991. Final Report 1992–95, NTEP No. 96-15; (Table 4); United States Department of Agriculture, Agricultural Research Service, Beltsville Agricultural Research Center, Beltsville, MD 20705.

TABLE 8

Mean number of mite-damaged leaves per zoysiagrass plant (N = 18)

| Cultivar | April 3, 1992 | April 24, 1992 | Combined Dates |
|---|---|---|---|
| DALZ9006 | 0.2a* | 0.2a | 0.2a |
| DALZ8508 | 0.7b | 0.6ab | 0.6b |
| DALZ8516 | 1.8d | 0.3ab | 1.0b |
| 'Emerald' | 1.3bc | 0.9b | 1.1b |
| DALZ8501 | 1.4cd | 2.6c | 2.0c |
| 'Crowne' | 5.4ef | 2.3c | 3.9d |
| 'El Toro' | 5.6ef | 2.8c | 4.2d |
| TC2033 | 4.4e | 4.3d | 4.4d |
| 'Palisades' | 7.5fg | 4.0cd | 5.8e |
| CD2031 | 7.6gh | 7.9e | 7.8f |
| Diamond | 7.8gh | 9.4ef | 8.6g |
| DALZ8701 | 9.3h | 9.4ef | 9.4g |
| 'Cavalier' | 9.1h | 9.8ef | 9.5g |
| 'Meyer' | 9.9h | 9.9ef | 9.9g |
| 'Belair' | 10.0h | 9.9f | 9.9g |
| JZ-1 | 10.0h | 9.9f | 10.0g |

*Data transformed using log (X + 0.5) for analysis. Means in a column followed by the same letter are not significantly different by Waller-Duncan k-ratio test (k = 100) (P = 0.05).
Reinert, J. A., M. C. Engelke, and S. J. Morton. 1993. Zoysiagrass resistance to the zoysiagrass mite, *Eriphyes zoysiae* (Acari: Eriophyidae). In R. N. Carrow, N. E. Christians, and R. C. Shermans (Eds.). International Turfgrass Society Research Journal 7. Intertec Publishing Corp., Overland Park, KS. pp. 349–352.

I claim:

1. A new and distinct cultivar of *Zoysia japonica* plant as herein shown and described.

* * * * *